United States Patent [19]

Obata et al.

[11] Patent Number: 5,081,144
[45] Date of Patent: Jan. 14, 1992

[54] PYRAZOLEOXIME DERIVATIVE AND INSECTICIDE, ACARICIDE AND FUNGICIDE

[75] Inventors: Tokio Obata; Katsutoshi Fujii; Yasuhisa Fukuda; Kiyoshi Tsutsumiuchi, all of Ube, Japan

[73] Assignee: Ube Industries, Ltd., Yamaguchi, Japan

[21] Appl. No.: 503,684

[22] Filed: Apr. 2, 1990

[30] Foreign Application Priority Data

Apr. 7, 1989 [JP] Japan ................................. 1-87036

[51] Int. Cl.⁵ .................... A01N 43/56; C07D 231/20
[52] U.S. Cl. ..................................... 514/407; 548/377
[58] Field of Search ........................ 548/377; 514/407

[56] References Cited

U.S. PATENT DOCUMENTS 4,843,068  6/1989  Hamaguchi et al. ............... 514/407

FOREIGN PATENT DOCUMENTS 63-183564  7/1988  Japan .

*Primary Examiner*—Robert W. Ramsuer
*Attorney, Agent, or Firm*—Frishauf, Holtz, Goodman & Woodward

[57] ABSTRACT

A compound represented by the formula:

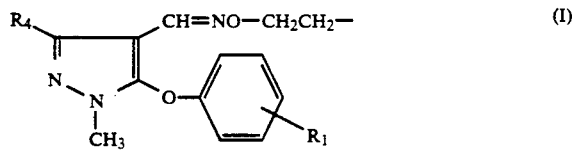

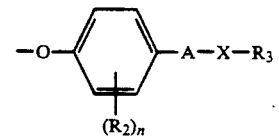

wherein $R_1$ represents hydrogen atom, a halogen atom or an alkyl group having 1 to 5 carbon atoms; $R_2$ represents hydrogen atom or an alkyl group having 1 to 5 carbon atoms; $R_3$ represents an alkyl group having 1 to 8 carbon atoms, an alkenyl group having 3 to 5 carbon atoms, an alkynyl group having 3 to 5 carbon atoms or an aralkyl group which may be also substituted; $R_4$ represents hydrogen atom or an alkyl group having 1 to 5 carbon atoms; n represents an integer of 4 and when $R_2$ is an alkyl group, n represents an integer of 1 to 3; A represents an alkylene group having 1 to 5 carbon atoms; and X represents an oxygen atom or a sulfur atom and an insecticide, acaricide or fungicide comprising a compound of the formula (I) as the active ingredient.

12 Claims, No Drawings

PYRAZOLEOXIME DERIVATIVE AND INSECTICIDE, ACARICIDE AND FUNGICIDE

BACKGROUND OF THE INVENTION

1. Field of the Invention

This invention relates to a novel pyrazoleoxime derivative and an insecticide, acaricide and fungicide containing the same as the active ingredient.

2. Background Information

As pyrazoleoxime derivatives, for example, Japanese Provisional Patent Publication No. 183564/1988 discloses compounds represented by the following formula:

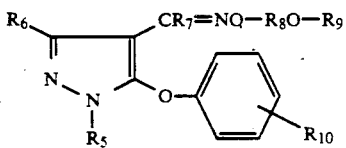

wherein $R_5$ represents an alkyl group; $R_6$ represents hydrogen atom or an alkyl group; $R_7$ represents hydrogen atom; $R_8$ represents an alkylene group; $R_9$ represents a group represented by the formula:

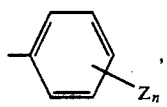

wherein Z represents hydrogen atom a halogen atom, an alkyl group, an alkyl group substituted by an alkoxy group, a group represented by the formula:

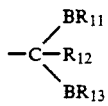

where $R_{11}$ and $R_{12}$ which may be the same or different and each represents an alkyl group, or $R_{11}$ and $R_{13}$ taken together may represent an alkylene group; $R_{12}$ represents an alkyl group; and B represents an oxygen atom or a sulfur atom; n represents an integer of 2 to 5, Z may be either the same or different); and $R_{10}$ represents hydrogen atom, an alkyl group or a halogen atom, as having insecticide, acaricide and fungicide activities, but these compounds cannot be hardly said to have sufficient activities.

SUMMARY OF THE INVENTION

An object of the present invention is to provide a novel pyrazoleoxime derivative and an insecticide, acaricide and fungicide containing the same as the active ingredient.

The present inventors have intensively studied in order to solve the problems as described above and consequently found that a novel pyrazoleoxime derivative has potent insecticide, acaricide and fungicide activity to accomplish the present invention.

More specifically, the present invention concerns: (1) a compound represented by the formula:

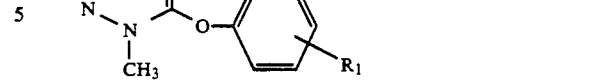

wherein $R_1$ represents hydrogen atom, a halogen atom or an alkyl group having 1 to 5 carbon atoms; $R_2$ represents a hydrogen atom or an alkyl group having 1 to 5 carbon atoms; $R_3$ represents an alkyl group having 1 to 8 carbon atoms, an alkenyl group having 3 to 5 carbon atoms, an alkynyl group having 3 to 5 carbon atoms or an aralkyl group which may be also substituted; $R_4$ represents hydrogen atom or an alkyl group having 1 to 5 carbon atoms; n represents an integer of 4 and when $R_2$ is an alkyl group, n represents an integer of 1 to 3; A represents an alkylene group having 1 to 5 carbon atoms; and X represents an oxygen atom or a sulfur atom; and (2) an insecticide, acaricide or fungicide comprising a compound of the formula (I) as the active ingredient.

DESCRIPTION OF THE PREFERRED EMBODIMENTS

In the novel pyrazoleoxime derivative (I) which is the title compound as mentioned above, as the alkyl group having 1 to 5 carbon atoms, straight or branched alkyl groups (e.g. methyl, ethyl, propyl, isopropyl, butyl, isobutyl, sec-butyl, t-butyl, pentyl, isopentyl and neopentyl) can be included.

As the alkyl group having 1 to 8 carbon atoms, straight or branched alkyl groups (in addition to the alkyl groups as exemplified above, for example, hexyl, 3-methylhexyl, 2-ethylhexyl, heptyl and octyl) can be included.

As the halogen atom, a fluorine atom, chlorine atom, bromine atom and iodine atom can be included. As the halo-lower alkyl group, alkyl groups having 1 to 2 carbon atoms substituted with 1 to 3 halogen atoms (e.g. chloromethyl, fluoromethyl, trifluoromethyl, 1-chloroethyl, 2-chloroethyl, 1-fluoroethyl and 2-fluoroethyl) can be included.

As the alkenyl group having 3 to 5 carbon atoms, straight or branched alkenyl groups (e.g. allyl, 1-propenyl, 1-butenyl, 2-butenyl, 1-methylallyl, 2-methylallyl, 2-pentenyl and isoprenyl) can be included.

As the alkynyl group having 3 to 5 carbon atoms, straight or branched alkynyl groups (e.g. 1-propynyl, 2-propynyl and 2-butynyl) can be included.

As the aralkyl group, for example, benzyl, 2-phenethyl, 4-chlorobenzyl, 4-fluorobenzyl, 4-methylbenzyl, 3,4-dichlorobenzyl and 2,4-difluorobenzyl can be included.

As the alkylene group having 1 to 5 carbon atoms, straight or branched alkylene groups (e.g. methylene, ethylene, trimethylene, 1-methylethylene, 2- methylethylene, tetramethylene, dimethylmethylene and pentamethylene) can be included.

As $R_1$, hydrogen atom, halogen atoms, alkyl groups having 1 to 5 carbon atoms, alkoxy groups having 1 to 5 carbon atoms and haloalkyl groups having 1 to 5 carbon atoms can be included, but hydrogen atom, halogen atoms and alkyl groups having 1 to 5 carbon atoms are preferred. More preferably, among halogen atoms, a fluorine atom or chlorine atom is preferred and among alkyl groups having 1 to 5 carbon atoms, a methyl group is preferred. As $R_2$, a hydrogen atom and alkyl groups having 1 to 5 carbon atoms can be included, but hydrogen atom and alkyl groups having 1 to 5 carbon atoms are preferred. More preferably, 0 among alkyl groups having 1 to 5 carbon atoms, a methyl group is preferred.

As $R_3$, alkyl groups having 1 to 8 carbon atoms, alkenyl groups having 3 to 5 carbon atoms, alkynyl groups having 3 to 5 carbon atoms and aralkyl groups which may be substituted can be included, but preferably alkyl groups having 1 to 4 carbon atoms (e.g. methyl, ethyl, propyl and isopropyl), alkenyl groups having 3 carbon atoms (e.g. allyl), alkynyl groups having 3 carbon atoms (e.g. 2-propynyl) and aralkyl groups which may be substituted (e.g. benzyl group) are preferred.

As $R_4$, a hydrogen atom and alkyl groups having 1 to 5 carbon atoms can be included. Among alkyl groups having 1 to 5 carbon atoms, methyl group and ethyl group are preferred.

As A, alkylene groups having 1 to 5 carbon atoms can be included, but alkylene groups having 1 to 2 carbon atoms (e.g. methylene and ethylene) are preferred.

As X, an oxygen atom and a sulfur atom can be included. n represents an integer of 4, and when $R_2$ is an alkyl group, n represents an integer of 1 to 3 and preferably 1 or 2.

As the novel pyrazoleoxime derivative (I) which is the title compound as described above, an E-isomer (syn-isomer), a Z-isomer (anti-isomer) and a mixture of an E-isomer and Z-isomer can be included, and further optical isomers based on the asymmetric carbon atom can be also included.

More specifically, as the most preferred title compound (I) of the present invention, compounds represented by the following formula can be included.

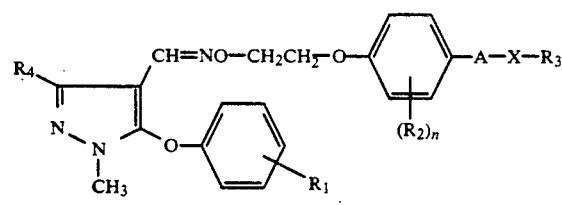

wherein $R_1$ represents a hydrogen atom, fluorine atom, chlorine atom or methyl group; R2 represents a hydrogen atom or methyl group; $R_3$ represents an alkyl group having 1 to 4 carbon atoms, an alkenyl group having 3 carbon atoms, an alkynyl group having 3 carbon atoms or an aralkyl group which may be also substituted; $R_4$ represents a hydrogen atom, methyl group or ethyl group; A represents an alkylene group having 1 to 2 carbon atoms; X represents an oxygen atom or a sulfur atom; and n represents an integer of 4 and when $R_2$ is methyl group, n represents an integer of 1 or 2.

The title compound (I) of the present invention can be prepared as shown in the following reaction schemes (in the following, three examples of preparation methods are shown).

(Preparation method )

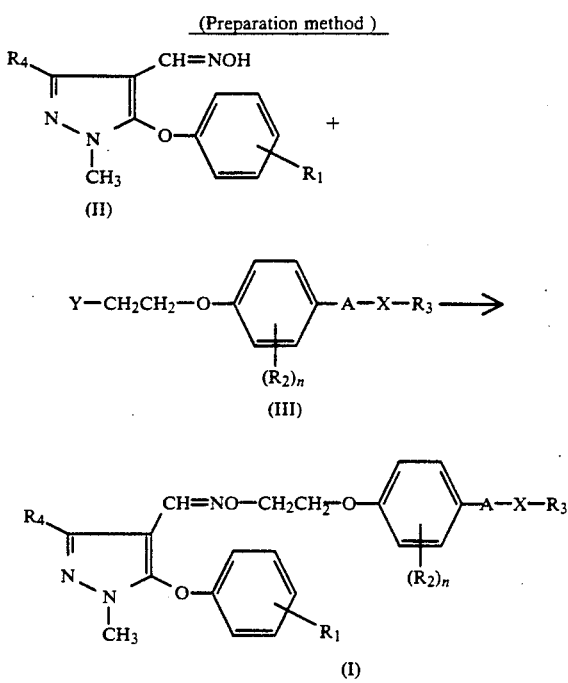

wherein $R_1$, $R_2$, $R_3$, $R_4$, n, A and X have the same meanings as defined above, and Y represents an eliminatable group.

Examples of the eliminatable group Y of the starting compound (III) are not particularly limited, and may include, for example, halogen atoms (chlorine, bromine or iodine), alkylthio groups (methylthio, ethylthio, propylthio and butylthio), alkanesulfonyloxy groups which may be substituted with halogen (methanesulfonyloxy, ethanesulfonyloxy and trifluoromethanesulfonyloxy), arylsulfonyloxy groups (benzenesulfonyloxy and p-toluenesulfonyloxy), hydroxyl group and so on, but a halogen atom is preferred.

The starting compound (II) can be synthesized easily as shown below according to the method as described in, for example, J. Org. Chem., 14, 783 (1949) or J. Am. Chem. Soc., 69, 1803 (1947) from a formyl derivative (IV) synthesized according to the method as described in C.A. 1970, 73, 3844W.

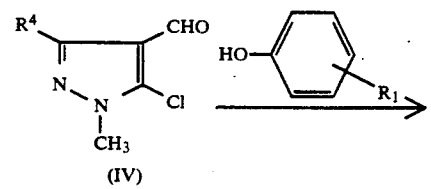

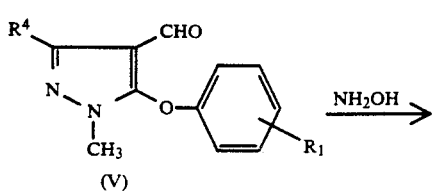

-continued

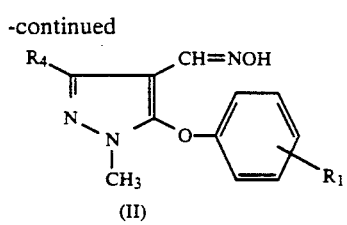

wherein R1 and R4 have the same meanings as defined above.

The starting compound (III) can be prepared easily as shown by the following reaction scheme according to the method as described in Organic Syntheses, Collective Volume 1, 435 (1941).

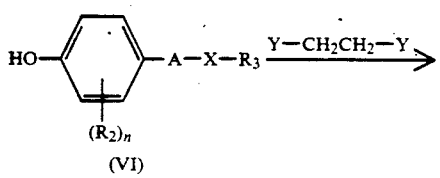

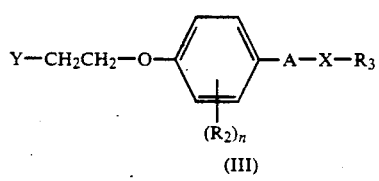

wherein $R_2$, $R_3$, A, X, n and Y have the same meanings as defined above.

The title compound (I) is preferably prepared generally by reacting the starting compound (II) and the starting compound (III) in a solvent in the presence of a base, and it can be also obtained by the reaction without addition of a base. Also, it can be obtained by reacting the starting compounds (II) and (III) by melting under heating in the absence of a solvent.

As the solvent, any solvent which does not interfere directly with the reaction can be used without particular limitation, including, for example, aromatic, aliphatic, alicyclic hydrocarbons with or without chlorination such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, tetrahydrofuran and dioxane; ketones such as acetone and methyl ethyl ketone; alcohols such as methanol, ethanol and ethylene glycol, or hydrated alcohols thereof; amides such as N,N-dimethylformamide and N,N-dimethylacetamide; organic bases such as pyridine, N,N-dimethylaniline and N,N-diethylaniline; 1,3-dimethyl-2-imidazolidinone; dimethyl sulfoxide; mixtures of the solvents as mentioned above; and the like.

When the reaction is carried out in a solvent mixture of the two-phase system, it is preferred to use a phase-transfer catalyst such as triethylbenzylammonium chloride or bromide, tetrabutylammonium chloride or bromide, and trioctylmethylammonium chloride.

As the base, for example, organic bases such as triethylamine, pyridine and N,N-diethylaniline; alkali metal alkoxides such as sodium methoxide and sodium ethoxide; inorganic bases such as sodium amide, sodium hydroxide, potassium hydroxide, potassium carbonate, sodium carbonate and sodium hydride can be included.

The method for preparing the title compound (I) can be performed at a reaction concentration of 5 to 100 %.

In the preparation method, the ratio of the starting compounds (II) and (III) can be such that 0.5 to 1.5 mole of the starting compound (III) is added to 1 mole of the starting compound (II), but 0.5 to 1.0 mole is preferred.

The reaction temperature is not particularly limited, provided that the reaction is carried out at the boiling point of the solvent used or lower, but generally the reaction is carried out at room temperature or higher, and it is preferred to shorten the reaction time by heating.

The reaction time may be variable depending on the concentration and the temperature as mentioned above, but the reaction can be carried out generally for 2 to 10 hours.

The title compound (I) can be purified suitable according to known means such as recrystallization and various chromatographies. Its acid addition salt can be easily obtained by, for example, introducing an acid into the reaction mixture after completion of the reaction, and then removing the solvent.

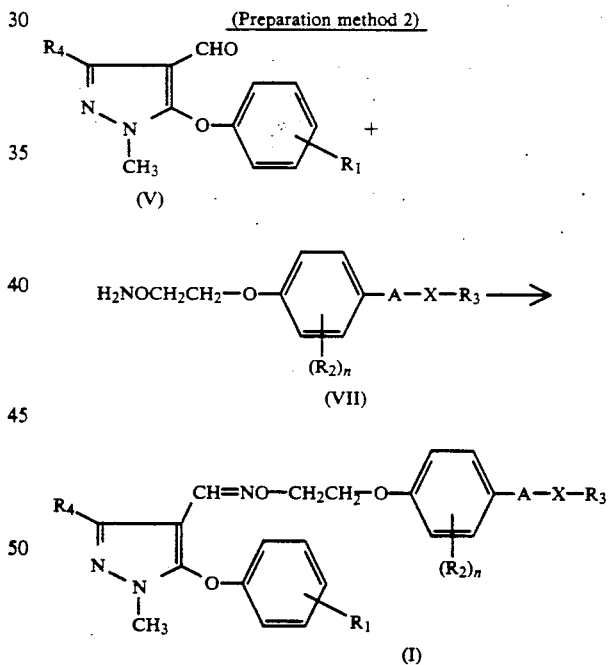

wherein $R_1$, $R_2$, $R_3$, $R_4$, n, A and X have the same meanings as defined above.

The reaction is generally carried out in the presence of a solvent, but the reaction between the compounds (V) and (VII) can be also carried out by hating in the absence of a solvent. As the solvent, those as mentioned above can be used.

The starting compound (VII) can be prepared easily according to the method as described in, for example, Methoden der Organischen Chemie (Hoben weyl) Band X/1, stickstoffverbindungen Teil I, P. 1192, as shown in the following reaction scheme.

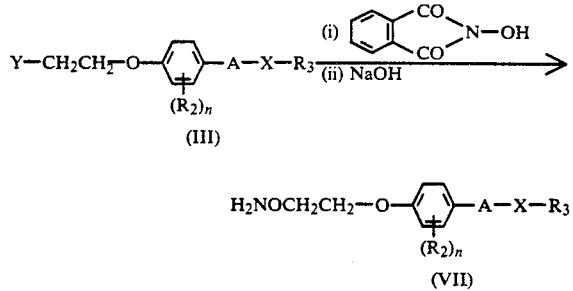

wherein $R_2$, $R_3$, A, X, n and Y have the same meanings as defined above.

The title compound (I) can be obtained in the preparation method 1, by using in place of the starting compound (II), using (VII) in place of the starting compound (III), and further carrying out the reaction similarly as in the preparation method 1 by use of (i) and (ii).

(Preparation method 3)

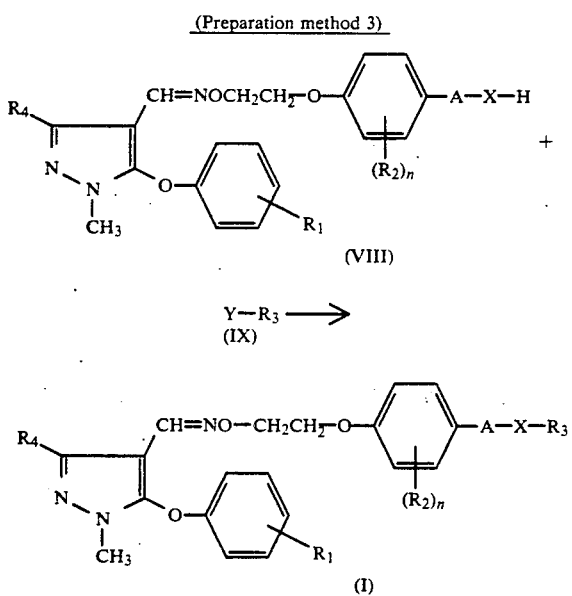

wherein $R_1$, $R_2$, $R_3$, $R_4$, n, A and X have the same meanings as defined above.

As is apparent from the above reaction scheme, since the compound H-Y is eliminated also in this reaction, the solvent, the base, etc. as shown in the preparation method 1 can be suitably used.

The title compound (I), in the preparation method 1, can be obtained by using the starting compound (VIII) in place of the starting compound (II), using the starting compound (IX) in place of the starting compound (III), and carrying out the reaction similarly as in the preparation method 1.

The title compound (I) obtained by the method as described above can be suitably purified according to known means such as recrystallization and various chromatographies.

The title compound (I) of the present invention exhibits remarkable insecticidal, acaricidal and fungicidal effects against injurious insects in agriculture and horticulture [for example, Hemiptera (planthoppers such as brown rice planthopper, leafhoppers such as green rice leafhopper, aphids and whiteflies); Lepidoptera (army- worms, diamondback moth, leafroller moths, pyralid moths, common cabbage worm); Coleoptera (e.g. weevils and leaf beetle); Acarina (citrus red mite and two-spotted spider mite)].

Further, it is effective for control of hygienically injurious insects such as flies, mosquitos and cockroaches.

Further, the compound (I) of the present invention has also activity against root-knot nematode, pine wood nematode and bulb mite in soil.

Also, the compound (I) of the present invention is effective for injurious diseases for agriculture and horticulture, and extremely effective for such diseases as rice blast, barley powdery mildew, cucumber downy mildew, cucumber gray mold and tomato late blight.

Thus, the compound (I) of the present invention has extremely wide scenes of uses, applications and high activity, and can be provided for practical application in various dosage forms.

The insecticide and fungicide of the present invention contain one or more of the compound (I) as the active ingredient.

The compound (I) can be also used alone, but it is generally preferable to use it with a carrier, a surfactant, a dispersing agent and an auxiliary agent, formulated therewith (for example, prepared as a composition such as powder, emulsion, fine granule, powder, wettable agent, oily suspension and aerosol).

As the carrier, for example, there can be included solid carriers such as talc, bentonite, clay, kaolin, diatomaceous earth, white carbon, vermicullite, slaked lime, siliceous sand, ammonium sulfate and urea; liquid carriers such as hydrocarbons (kerosine, mineral oil), aromatic hydrocarbons (benzene, toluene, xylene), chlorinated hydrocarbons (chloroform, carbon tetrachloride), ethers (dioxane, tetrahydrfuran), ketones (acetone, cyclohexanone, isophorone), esters (ethyl acetate, ethylene glycol acetate, dibutyl maleate), alcohols (methanol, n-hexanol, ethylene glycol), polar solvents (dimethylformamide, dimethyl sulfoxide) and water; gas carriers such as air, nitrogen, carbon dioxide, Freon (in this case, can be jetted as mixture); and the like.

As the surfactant and the dispersing agent which can be used for improvement of attachment, absorption of the present agent onto animals or vegetables or improvement of such performances of the chemical as dispersion, emulsification and spreding, for example, alcohol sulfates, alkylsulfonic acid salts, ligninsulfonic acid salts and polyoxyethylene glycol ether can be included. For improvement of the properties of the preparation, carboxymethyl cellulose, polyethylene glycol and gum arabic can be used as the auxiliary agent.

In the preparation of the present agent, the carrier, the surfactant, the dispersing agent and the auxiliary agent can be used either singly or in a suitable combination depending on the respective purposes.

The effective component concentration when the compound (I) of the present invention is formed into a preparation may be generally 1 to 50% by weight in emulsion, generally 0.3 to 25% by weight in powder, generally 1 to 90% by weight in wettable agent, generally 0.5 to 5% by weight in granule, generally 0.5 to 5% by weight in oil and generally 0.1 to 5 % by weight in aerosol.

These preparations can be diluted to appropriate concentration and can be provided for various uses by spraying onto vegetable stalks and leaves, soil, the water surface of a paddy field, or by direct application.

EXAMPLES

The present invention is described by referring to the Examples. However, these Examples are not limitative of the present invention.

EXAMPLES 1

Synthesis of 1,3-dimethyl-5-phenoxypyrazole-4-formaldoxime 0-2-[4-(2-methoxyethyl)phenoxy]ethyl ether To a solution of 1,3-dimethyl-5-phenoxypyrazole-4-formaldoxime which is the starting compound (II) (1.1 g, 5.0 mmole) and 2-[4-(2-methoxyethyl)phenoxy]ethyl bromide which is the starting compound (III) (1.3 g, 5.0 mmole) dissolved in dimethyl sulfoxide (30 ml) was added potassium hydroxide (0.4 g) at room temperature under stirring, followed further by stirring at room temperature for 5 hours.

After completion of the reaction, water was added, and the oily product separated was extracted with ethyl acetate. The extract was washed with water, dried over anhydrous sodium sulfate, and the solvent was evaporated under reduced pressure.

The oily product obtained was isolated by silica gel column chromatography (Wako Gel C-200, eluted with hexane : ethyl acetate =5 : 1) to give 1.5 g of the title compound (I) (Compound No. 1) as a colorless oily product.

$n_D^{25.6} = 1.5635$

Synthesis of 1,3-dimethyl-5-(4-fluorophenoxy)pyrazole-4-formaldoxime 0-2-[4-(2-ethoxyethy)phenoxy]ethyl ether To a solution of 1,3-dimethyl-5-(4-fluorophenoxy)-pyrazole-4-formaldoxime which is the starting compound (II) (1.2 g, 5.1 mmole) and 2-[4-(2-ethoxyethyl)-phenoxy]ethyl bromide which is the starting compound (III) (1.4 g, 5.1 mmole) dissolved in dimethylformamide (30 ml) was added potassium hydroxide (0.4 g) at room temperature under stirring, followed further by stirring at room temperature to 40° C. for 4 hours.

After completion of the reaction, water was added, and the oily product separated was extracted with ethyl acetate. The extract was washed with water, dried over anhydrous sodium sulfate, and the solvent was evaporated under reduced pressure.

The oily product obtained was isolated by silica gel column chromatography (Wako Gel C-200, eluted with hexane : ethyl acetate =5 : 1) to give 1.6 g of the title compound (I) (Compound No. 2) as a colorless oily product.

$n_D^{24.4} = 1.5482$

EXAMPLE 3 to 39

In Example 2, by use of the starting compound (II):

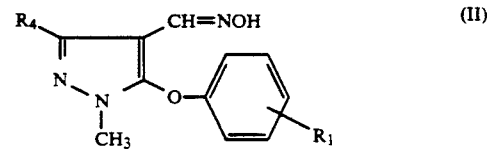

$R_1$ and $R_4$ are the same as shown in Table 1. and the starting compound (III):

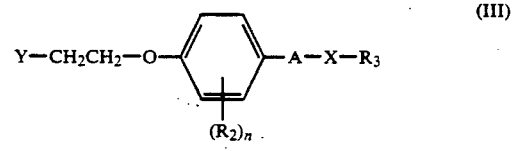

$R_2$, $R_3$, X, Y, A and n are the same as shown in Table 1, and carrying out otherwise the same procedure as in Example 2, the title compounds (I) shown in Table 1 were obtained (the numbers of the respective compounds are shown by 3 to 39 corresponding to Examples. Also, as Comparative examples for the compounds of the present invention, the compounds disclosed in Japanese Provisional Patent Publication No. 183564/1988 are listed together.).

TABLE 1

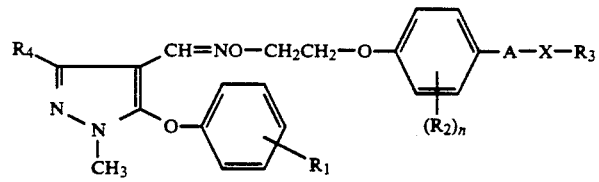

| No. | $-R_1$ | $-(R_2)_n$ | A | $-X-R_3$ | $-R_4$ | Physical property |
|---|---|---|---|---|---|---|
| 1 | H | H | $-CH_2CH_2-$ | $-OCH_3$ | $CH_3$ | $n_D^{25.6}$ 1.5635 |
| 2 | 4-F | H | $-CH_2CH_2-$ | $-OC_2H_5$ | $CH_3$ | $n_D^{24.4}$ 1.5482 |
| 3 | H | 2-$CH_3$ | $-CH_2CH_2-$ | $-OC_2H_5$ | $CH_3$ | $n_D^{25.6}$ 1.5545 |
| 4 | H | 2,6-$(CH_3)_2$ | $-CH_2CH_2-$ | $-OC_2H_5$ | $CH_3$ | $n_D^{25.6}$ 1.5469 |
| 5 | 4-F | 2-$CH_3$ | $-CH_2CH_2-$ | $-OC_2H_5$ | $CH_3$ | $n_D^{25.6}$ 1.5417 |
| 6 | 4-F | 2,6-$(CH_3)_2$ | $-CH_2CH_2-$ | $-OC_2H_5$ | $CH_3$ | $n_D^{25.6}$ 1.5392 |
| 7 | H | H | $-CH_2CH_2-$ | $-OC_2H_5$ | $CH_3$ | $n_D^{24.3}$ 1.5584 |
| 8 | H | H | $-CH_2CH_2-$ | $-OC_3H_7$-n | $CH_3$ | $n_D^{21.8}$ 1.5532 |
| 9 | H | H | $-CH_2CH_2-$ | $-OC_3H_7$-i | $CH_3$ | |
| 10 | H | H | $-CH_2CH_2-$ | $-OC_4H_9$-n | $CH_3$ | $n_D^{23.2}$ 1.5514 |
| 11 | H | H | $-CH_2CH_2-$ | $-OCH_2CH=CH_2$ | $CH_3$ | $n_D^{21.2}$ 1.5626 |
| 12 | H | H | $-CH_2CH_2-$ | $-OCH_2C\equiv CH$ | $CH_3$ | $n_D^{21.2}$ 1.5690 |

TABLE 1-continued $$R_4-\underset{\underset{CH_3}{N}}{\overset{CH=NO-CH_2CH_2-O-\phenyl(R_2)_n-A-X-R_3}{\diagup}}\diagdown N\diagdown_{O-\phenyl-R_1}$$

| No. | —R₁ | —(R₂)ₙ | A | —X—R₃ | —R₄ | Physical property |
|---|---|---|---|---|---|---|
| 13 | H | H | —CH₂CH₂— | —OCH₂—phenyl | CH₃ | $n_D^{21.9}$ 1.5819 |
| 14 | 4-F | H | —CH₂CH₂— | —OCH₃ | CH₃ | $n_D^{19.6}$ 1.5517 |
| 15 | 4-CH₃ | H | —CH₂CH₂— | —OC₂H₅ | CH₃ | $n_D^{23.4}$ 1.5576 |
| 16 | 4-OCH₃ | H | —CH₂CH₂— | —OC₂H₅ | CH₃ | |
| 17 | 4-Cl | H | —CH₂CH₂— | —OC₂H₅ | CH₃ | $n_D^{27.4}$ 1.5638 |
| 18 | 4-CF₃ | H | —CH₂CH₂— | —OC₂H₅ | CH₃ | |
| 19 | H | H | —CH(CH₃)—CH₂— | —OC₂H₅ | CH₃ | |
| 20 | H | H | —CH₂—CH(CH₃)— | —OC₂H₅ | CH₃ | |
| 21 | H | H | —(CH₂)₃— | —OC₂H₅ | CH₃ | |
| 22 | H | H | —(CH₂)₃— | —OCH₃ | CH₃ | |
| 23 | H | H | —(CH₂)₄— | —OCH₃ | CH₃ | |
| 24 | H | H | —CH₂CH₂— | —SCH₃ | CH₃ | $n_D^{27.2}$ 1.5825 |
| 25 | H | H | —CH₂CH₂— | —SC₂H₅ | CH₃ | |
| 26 | 3-Cl | H | —CH₂CH₂— | —OC₂H₅ | CH₃ | |
| 27 | H | H | —CH₂— | —OC₂H₅ | CH₃ | $n_D^{23.0}$ 1.5638 |
| 28 | H | H | —CH₂— | —OC₃H₇-n | CH₃ | |
| 29 | 4-F | H | —CH₂— | —OC₂H₅ | CH₃ | $n_D^{24.6}$ 1.5525 |
| 30 | 4-Cl | H | —CH₂CH₂— | —OCH₂CH=CH₂ | C₂H₅ | $n_D^{27.2}$ 1.5622 |
| 31 | 4-Cl | H | —CH₂CH₂— | —OC₂H₅ | C₂H₅ | $n_D^{27.2}$ 1.5539 |
| 32 | H | 2-CH₃ | —CH₂CH₂— | —OC₂H₅ | H | $n_D^{21.4}$ 1.5534 |
| 33 | H | H | —CH₂CH₂— | —OC₂H₅ | H | $n_D^{21.6}$ 1.5530 |
| 34 | H | H | —CH₂CH₂— | —OCH₃ | H | $n_D^{21.6}$ 1.5622 |
| 35 | H | H | —CH₂CH₂— | —OCH₃ | C₂H₅ | |
| 36 | H | H | —CH₂CH₂— | —OC₂H₅ | C₂H₅ | |
| 37 | 4-F | H | —CH₂CH₂— | —OCH₃ | C₂H₅ | |
| 38 | 4-F | H | —CH₂CH₂— | —OC₂H₅ | C₂H₅ | |
| 39 | 4-F | H | —CH₂CH₂— | —OCH₃ | H | |
| Comparative | H | H | H | — | CH₃ | $n_D^{24.2}$ 1.5730 |

EXAMPLE 40

Preparation of granules

5 Parts by weight of the compound of Compound No. 1 (the compound of Example 1), 35 parts by weight of bentonite, 57 parts by weight of talc, 1 part by weight of Neopelex Powder (trade name: Kao-Atlas) and 2 parts by weight of lignin sulfonate were uniformly mixed, and subsequently kneaded with addition of a small amount of water, followed by granulation and drying to give granules.

EXAMPLE 41

Preparation of wettable agent

10 Parts by weight of the compound of Compound No. 4 (the compound of Example 4), 70 parts by weight of kaolin, 18 parts by weight of white carbon, 1.5 parts by weight of Neopelex Powder (trade name: Kao-Atlas) and 0.5 part by weight of Demol (trade name: Kao Atlas) were uniformly mixed, followed by pulverization to give a wettable agent.

EXAMPLE 42 Preparation of emulsion

To 20 parts by weight of the compound of Compound No. 4 and 70 parts by weight of xylene was added 10 parts by weight of Toxanone (trade name: Sanyo Kasei Kogyo).

EXAMPLE 43

Preparation of powder

Parts by weight of Compound No. 6, 50 parts by weight of talc and 45 parts by weight of kaolin were uniformly mixed to give powder.

EXAMPLE 44

Activity test against diamondback moth

Each wettable agent of the title compound (I) shown in Table 1 prepared according to Example 40 was diluted to 50 ppm with water containing a surfactant (0.01%), and each cabbage leaf strip (5 cm × 5 cm) was dipped in each chemical solution for 30 seconds, dried on air and then placed in a plastic cup.

And, ten 3rd instar diamondback moth larvae were freed, and the plastic cup was closed with a lid and left to stand in a thermostatic chamber of 25° C. for 2 days. The numbers of live and dead larvae were counted to determine the lethality.

Evaluation of the drug is shown by the 4 ranks according to the range of lethality (A: 100%, B: 99 to 80%, C: 79 to 60% D: 59% or lower).

The results are shown in Table 2.

TABLE 2

| Compound No. | Acitivity against diamondback moth |
|---|---|
| 1 | A |
| 2 | A |
| 7 | A |
| 10 | B |
| 11 | B |
| 12 | B |
| 14 | A |
| 15 | B |
| 17 | A |
| 24 | A |
| 27 | A |
| 29 | A |
| 30 | B |
| 31 | A |

EXAMPLE 45

Activity against green rice leafhopper

Each wettable agent of the title compounds (I) shown in Table 1 prepared similarly as described in Example 40 was diluted with water containing a surfactant (0.01%) to 100 ppm to prepare a chemical solution. In each chemical solution was dipped young rice seedlings for 30 seconds, and the rice seedlings after air drying were inserted into the respective glass cylinders.

And, ten 4th instar green rice leafhopper nymphs were freed into the cylinder, and the cylinder was left to stand stoppered with a porous plug in a thermostat chamber of 25° C. for 4 days. The numbers of live and dead nymphs in each cylinder were counted to determine the lethality.

The results are shown in Table 3 according to the evaluation method of 4 ranks shown in Example 44.

TABLE 3

| Compound No. | Activity against green rice leafhopper |
|---|---|
| 1 | A |
| 2 | A |
| 5 | B |
| 7 | A |
| 8 | A |
| 11 | A |
| 12 | A |
| 14 | A |
| 15 | A |
| 17 | A |
| 24 | A |
| 27 | A |
| 29 | A |
| 30 | B |
| 31 | A |

EXAMPLE 46

Activity test against female adult of twospotted spider mite

Each wettable agent of the title compounds (I) shown in Table 1 prepared similarly as in Example 41 was diluted with water containing a surfactant (0.1%) to 30 ppm and 10 ppm, and each kidney beans leaf disk (diameter 20 mm) having ten female adult of twospotted spider mites infested thereon was dipped in each chemical solution (30 ppm and 10 ppm) for 15 seconds.

Next, each of these leaf disks was left to stand in a thermostatic chamber of 25° C., and the numbers of live and dead mites on each leaf disk after 3 days were counted to determine the lethality.

The results are shown in Table 4 [the Comparative chemical used is the compound described in the column of Comparative example in Table 1 (the compound disclosed in Japanese Unexamined Patent Publication No. 183564/1988) prepared similarly].

TABLE 4

$$CH_3 \text{-pyrazole-} CH=NOCH_2CH_2-O-\text{phenyl, } O-\text{phenyl, } N-CH_3$$

| Compound No. | Lethality (%) 30 ppm | Lethality (%) 10 ppm |
|---|---|---|
| 1 | 100 | 100 |
| 2 | 100 | 100 |
| 3 | 100 | 100 |
| 5 | 100 | 100 |
| 7 | 100 | 100 |
| 8 | 100 | 100 |
| 10 | 100 | 100 |
| 11 | 100 | 100 |
| 12 | 100 | 100 |
| 14 | 100 | 100 |
| 15 | 100 | 100 |
| 17 | 100 | 100 |
| 24 | 100 | 100 |
| 29 | 100 | 100 |
| Comparative chemical | 62 | 35 |

EXAMPLE 47

Activity test against female adult of citrus red mite

Each wettable agent of the title compounds (I) shown in Table 1 prepared similarly as in Example 41 was diluted with water containing a surfactant (0.01%) to 10 ppm and 3 ppm) was sprayed in 5 ml on each mulberry leaf disk (diameter 20 mm) having 10 female adult of citrus red mites infested thereon.

Next, each of these leaf disks was left to stand in a thermostatic chamber of 25° C., and the numbers of live and dead mites on each mulberry leaf disk after 3 days were counted to determine the lethality.

The results are shown in Table 5 (the Control chemical used is the compounds described in the column of Comparative example in Table 1 prepared similarly).

TABLE 5

| Compound No. | Lethality (%) 10 ppm | Lethality (%) 3 ppm |
|---|---|---|
| 1 | 100 | 100 |
| 2 | 100 | 100 |
| 3 | 100 | 100 |
| 5 | 100 | 100 |
| 7 | 100 | 100 |
| 8 | 100 | 100 |
| 10 | 100 | 100 |
| 11 | 100 | 100 |
| 12 | 100 | 100 |
| 14 | 100 | 100 |
| 15 | 100 | 100 |
| 17 | 100 | 100 |

TABLE 5-continued

| Compound No. | Lethality (%) | |
|---|---|---|
| | 10 ppm | 3 ppm |
| 24 | 100 | 100 |
| 27 | 100 | 100 |
| 29 | 100 | 100 |
| Comparative chemical | 100 | 16 |

EXAMPLE 48

Control activity test (preventive effect) against rice blast

In each plastic planting pot of 6 cm in diameter were grown 10 rice seedlings (species: Nipponbare), and onto the 2.5-leaf stage young plant was sprayed each wettable agent of the title compounds (I) shown in Table 1 prepared similarly as in Example 41, diluted to 500 ppm with water containing a surfactant (0.01%), in 10 ml per one pot.

After spraying, the plants were grown for 2 days in a glass greenhouse, and then a suspension of conidiospores of rice blast (*Pyricularia oryzae*) (7 × 10⁴ spores/ml) prepared from afflicted leaves was inoculated by spraying uniformly on the plant leave.

After inoculation, the plant was grown in a humid chamber at 28 C. for 5 days, and the extend of the rice blast lesion appearing on the leave was examined.

Evaluation of the chemical effect was shown by 6 ranks as compared with the extent of the lesion of the non-treated group (0: afflicted wholly, 1: about 60% of lesion area, 2: about 40% of lesion area, 3: about 20% of lesion area, 4: about 10% of lesion area, 5: no lesion).

The results are shown in Table 6 (the Control chemical used is the compound described in the column of Comparative example in Table 1 similarly prepared).

TABLE 6

| Compound No. | Preventive effect against rice blast |
|---|---|
| 10 | 4 |
| 17 | 4 |
| 27 | 5 |
| 30 | 4 |
| 31 | 4 |
| Comparative chemical | 0 |
| Non-treatment | 0 |

EXAMPLE 49

Control activity test (prevention effect) against barley powdery mildew

Ten barleys (species: black barley) were grown in each plastic planting pot of 6 cm in diameter, and onto the 1.5-leaf stage young plant was sprayed each wettable agent of the title compounds (I) shown in Table 1 prepared similarly as in Example 41, diluted to 500 ppm with water containing a surfactant (0.01%), in 10 ml per pot.

After spraying, the plants were grown in a glass greenhouse for 2 days, and then a suspension of conidiospores of barley powdery mildew (*Erysiphe graminis*) prepared from afflicted leaves was inoculated by spraying on the plants uniformly.

After inoculation, the plants were grown in the glass greenhouse for one week, and the extent of the barley powdery mildew lesion appearing on the first leaf was examined.

The results of judgement of the chemical effects are shown in Table 7 according to the same evaluation method as in Example 48 (the Comparative chemical used is the compound described in the column of Comparative example in Table 1 prepared similarly).

TABLE 7

| Compound No. | Preventive effect against barley powdery mildew |
|---|---|
| 1 | 5 |
| 2 | 5 |
| 3 | 4 |
| 5 | 4 |
| 7 | 5 |
| 10 | 4 |
| 11 | 5 |
| 12 | 5 |
| 14 | 5 |
| 15 | 5 |
| 17 | 5 |
| 24 | 4 |
| 27 | 5 |
| 29 | 5 |
| 30 | 4 |
| 31 | 4 |
| Comparative chemical | 1 |
| Non-treatment | 0 |

According to the present invention, pyrazoleoxime derivatives having excellent insecticide, acaricide and fungicide effects can be provided.

We claim:

1. A compound represented by the formula:

$$\underset{CH_3}{\underset{|}{N}}\underset{N}{\overset{R_4}{\underset{\|}{C}}}\overset{CH=NO-CH_2CH_2-}{\underset{O}{\overset{|}{C}}}\underset{R_1}{\bigcirc} \quad (I)$$

$$-O-\underset{(R_2)_n}{\bigcirc}-A-X-R_3$$

wherein $R_1$ represents a hydrogen atom, a chlorine atom, a fluorine atom or an alkyl group having 1 to 5 carbon atoms;

$R_2$ represents a hydrogen atom or an alkyl group having 1 to 5 carbon atoms;

$R_3$ represents an alkyl group having 1 to 5 carbon atoms, an alkenyl group having 3 to 5 carbon atoms or an alkynyl group having 3 to 5 carbon atoms;

$R_4$ represents a hydrogen atom or an alkyl group having 1 to 5 carbon atoms;

n is 4, but when $R_2$ is an aklyl group, n is 1;

A represents an alkylene group having 1 to 5 carbon atoms and X represents an oxygen atom or a sulfur atom.

2. The compound according to claim 1 wherein said $R_1$ is selected from the group consisting of a hydrogen atom, fluorine atom, chlorine atom and methyl group.

3. The compound according to claim 1, wherein said $R_2$ is selected from the group consisting of a hydrogen atom and a methyl group.

4. The compound according to 1, wherein said $R_3$ is selected from the group consisting of a methyl group; ethyl group, propyl group, isopropyl group, butyl group, allyl group and 2-propynyl group.

5. The compound according to claim 1, wherein said R4 selected from the group consisting of a methyl group and an ethyl group.

6. The compound according to claim 1, wherein said aklylene group is selected from the group consisting of a methylene group and an ethylene group.

7. The compound according to claim 1, wherein said compound is an E-isomer (syn-isomer), a Z-isomer (anti-isomer) or a mixture of E-isomer and a Z-isomer, or optical isomers based on the asymmetric carbon atom.

8. The compound according to claim 1, wherein said compound is represented by the following formula:

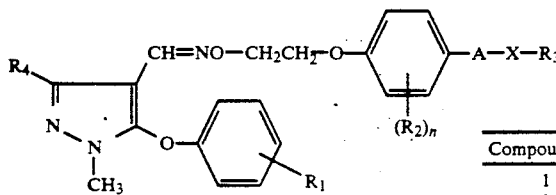

wherein $R_1$ represents a hydrogen atom, a fluorine atom, a chlorine atom or a methyl group;

$R_2$ represents a hydrogen atom or a methyl group;

$R_3$ represents an alkyl group having 1 to 4 carbon atoms, an alkenyl group having 3 carbon atoms or an alkynyl group having 3 carbon atoms;

$R_4$ represents a hydrogen atom, a methyl group or an ethyl group;

A represents an alkylene group having 1 to 2 carbon atoms;

X represents an oxygen atom or a sulfur atom; and n is 4, but when $R_2$ is a methyl group, n is 1.

9. An insecticide, acaricide or fungicide comprising an effective amount of a compound of the formula (I) according to claim 1 as the active ingredient and a carrier.

10. The compound according to claim 1, wherein the compound is selected from the group, consisting of compounds set forth below:

| Compound No. | $-R_1$ | $-(R_2)_n$ | A | $-X-R_3$ | $-R_4$ |
|---|---|---|---|---|---|
| 1 | H | H | $-CH_2CH_2-$ | $-OCH_3$ | $CH_3$ |
| 2 | 4-F | H | $-CH_2CH_2-$ | $-OC_2H_5$ | $CH_3$ |
| 3 | H | 2-$CH_3$ | $-CH_2CH_2-$ | $-OC_2H_5$ | $CH_3$ |
| 5 | 4-F | 2-$CH_3$ | $-CH_2CH_2-$ | $-OC_2H_5$ | $CH_3$ |
| 7 | H | H | $-CH_2CH_2-$ | $-OC_2H_5$ | $CH_3$ |
| 8 | H | H | $-CH_2CH_2-$ | $-OC_3H_7$-n | $CH_3$ |
| 9 | H | H | $-CH_2CH_2-$ | $-OC_3H_7$-i | $CH_3$ |
| 10 | H | H | $-CH_2CH_2-$ | $-OC_4H_9$-n | $CH_3$ |
| 11 | H | H | $-CH_2CH_2-$ | $-OCH_2CH=CH_2$ | $CH_3$ |
| 12 | H | H | $-CH_2CH_2-$ | $-OCH_2C\equiv CH$ | $CH_3$ |
| 14 | 4-F | H | $-CH_2CH_2-$ | $-OCH_3$ | $CH_3$ |
| 15 | 4-$CH_3$ | H | $-CH_2CH_2-$ | $-OC_2H_5$ | $CH_3$ |
| 17 | 4-Cl | H | $-CH_2CH_2-$ | $-OC_2H_5$ | $CH_3$ |
| 18 | 4-$CF_3$ | H | $-CH_2CH_2-$ | $-OC_2H_5$ | $CH_3$ |
| 19 | H | H | $-CH-CH_2-$<br>$\quad\vert$<br>$\quad CH_3$ | $-OC_2H_5$ | $CH_3$ |
| 20 | H | H | $-CH_2-CH-$<br>$\qquad\vert$<br>$\qquad CH_3$ | $-OC_2H_5$ | $CH_3$ |
| 21 | H | H | $-(CH_2)_3-$ | $-OC_2H_5$ | $CH_3$ |
| 22 | H | H | $-(CH_2)_3-$ | $-OCH_3$ | $CH_3$ |
| 23 | H | H | $-(CH_2)_4-$ | $-OCH_3$ | $CH_3$ |
| 24 | H | H | $-CH_2CH_2-$ | $-SCH_3$ | $CH_3$ |
| 25 | H | H | $-CH_2CH_2-$ | $-SC_2H_5$ | $CH_3$ |
| 26 | 3-Cl | H | $-CH_2CH_2-$ | $-OC_2H_5$ | $CH_3$ |
| 27 | H | H | $-CH_2-$ | $-OC_2H_5$ | $CH_3$ |
| 28 | H | H | $-CH_2-$ | $-OC_3H_7$-n | $CH_3$ |
| 29 | 4-F | H | $-CH_2-$ | $-OC_2H_5$ | $CH_3$ |
| 30 | 4-Cl | H | $-CH_2CH_2-$ | $-OCH_2CH=CH_2$ | $C_2H_5$ |
| 31 | 4-Cl | H | $-CH_2CH_2-$ | $-OC_2H_5$ | $C_2H_5$ |
| 32 | H | 2-$CH_3$ | $-CH_2CH_2-$ | $-OC_2H_5$ | H |
| 33 | H | H | $-CH_2CH_2-$ | $-OC_2H_5$ | H |
| 34 | H | H | $-CH_2CH_2-$ | $-OCH_3$ | H |
| 35 | H | H | $-CH_2CH_2-$ | $-OCH_3$ | $C_2H_5$ |

11. The compound according to claim 10, wherein the compound is selected from the group consisting of compound numbers 1, 2, 3, 5, 7, 8, 10, 11, 12, 14, 15, 17, 24 and 29.

12. A method for combatting acarids comprising applying to acarids or to a locus thereof an acaricidally effective amount of a compound according to claim 1.

* * * * *